(12) United States Patent  (10) Patent No.: US 8,951,273 B1
Fard  (45) Date of Patent: Feb. 10, 2015

(54) SURGICAL INSTRUMENT FOR ENDOSCOPIC SURGICAL PROCEDURES

(76) Inventor: Mike Fard, Charlottesville, VA (US)

( * ) Notice: Subject to any disclaimer, the term of this patent is extended or adjusted under 35 U.S.C. 154(b) by 534 days.

(21) Appl. No.: 12/891,307

(22) Filed: Sep. 27, 2010

Related U.S. Application Data

(60) Provisional application No. 61/245,836, filed on Sep. 25, 2009.

(51) Int. Cl.
*A61B 17/3209* (2006.01)
*A61B 1/313* (2006.01)

(52) U.S. Cl.
USPC ............ 606/170; 600/104; 600/183; 600/204

(58) Field of Classification Search
USPC ........... 606/167–180, 190; 600/104, 183, 204
See application file for complete search history.

(56) References Cited

U.S. PATENT DOCUMENTS

| | | | | |
|---|---|---|---|---|
| 2,136,414 A * | 11/1938 | Clements | ...................... | 606/174 |
| 5,306,284 A * | 4/1994 | Agee et al. | ..................... | 606/170 |
| 5,772,676 A * | 6/1998 | Cuschieri et al. | ............. | 606/167 |
| 5,899,912 A * | 5/1999 | Eaves, III | ....................... | 606/159 |
| 7,004,173 B2 * | 2/2006 | Sparks et al. | .................. | 128/898 |
| 7,163,532 B2 * | 1/2007 | Zinkel | ................. | 606/1 |
| 7,780,690 B2 * | 8/2010 | Rehnke | .......................... | 606/170 |
| 2007/0288043 A1 * | 12/2007 | Rehnke | .......................... | 606/170 |
| 2008/0195128 A1 * | 8/2008 | Orbay et al. | .................. | 606/170 |

* cited by examiner

*Primary Examiner* — Kathleen Holwerda

(74) *Attorney, Agent, or Firm* — Sheldon H. Parker, Esq.

(57) ABSTRACT

A surgical instrument for endoscopic surgery having a solid or transparent body and open windows on each of the opposing sides at the distal end, proximate a top open region. The open windows can be arcs or other configurations either open or with bars which are generally integral with the top and extend across the windows. An integrated tissue retractor spring, once activated, extends above the open region and when not activated rests within the open region. A marking member, that can be in fluid contact with a marking reservoir, can be placed at the distal end of the body. In another embodiment the body can be curved using a flexible blade shaft. In a further embodiment the handle has a linear body, containing a blade activation mechanism, at least one activation trigger, and a connector means.

16 Claims, 17 Drawing Sheets

SURGICAL INSTRUMENT FOR ENDOSCOPIC SURGICAL PROCEDURES

CROSS REFERENCE TO PRIOR APPLICATIONS

This application is a non-provisional of Ser. No. 61/245,836 filed Sep. 25, 2009 which is incorporated herein as though recited in full.

FIELD OF THE INVENTION

The invention relates to a surgical instrument, specifically a novel instrument for increased visibility and ease of endoscopic procedures.

BACKGROUND OF INVENTION

In the U.S., nearly 12.3 million specialty endoscopic procedures were performed in 2005. The U.S. market for specialty endoscopic surgery products—including those used in arthroscopic, endovascular, gastrointestinal, neurologic, otorhinolaryngologic, and thoracoscopic procedures was valued at approximately $1.7 billion in 2005. Growing at a compound annual rate of 9.3%, sales of these products are projected to reach an estimated $3.8 billion in the year 2014 (source: medtechinsight.com).

The advantages of endoscopic surgery over open surgery include lower overall treatment costs, reduced patient trauma, shorter hospital stays, and faster recovery times. These benefits have resulted in the conversion of many types of open surgery procedures to endoscopic procedures, a continuing trend that is being driven by advancements in the array of endoscopic surgery products that includes access devices, endoscopes, hand instruments, electrosurgery systems, and fluid management systems, among others.

Carpal tunnel is formed by an arch of the eight wrist bones, spanned on its palmar surface by the transverse carpal ligament, the flexor retinaculum. The carpal tunnel functions as a large mechanical pulley to provide the appropriate moment arms for the digital flexor tendons as they pass through the tunnel. The tendons can then transmit force out in to the fingers and impart only an appropriate amount of tension to develop torque at the level of the wrist.

Within the carpal tunnel these tendons are lubricated and nourished by two synovial membranes—the radial and ulnar bursa. The medial nerve also shares the carpal tunnel, and then branches out to provide sensory innovation to the palmar surfaces of the thumb, index, long and a portion of the ring finger. In addition, a small motor branch of the medial nerve supplies the thenar muscles, which are responsible for lifting the thumb in to opposition with the fingers.

Carpal tunnel syndrome describes numerous clinical signs and symptoms resulting from pressure on the medial nerve inside the carpal tunnel. The typical etiology is increased pressure within the carpal tunnel, which interferes with the function of the medial nerve. The patient experiences numbness and tingling in the fingers, together with pain that may radiate as far as shoulder or base of the neck. Other symptoms include: impaired grasping ability, due to sensory deprivation from the figures; loss of sleep from pain and numbness in the hand; and weakness or atrophy of the thenar muscles.

The pathology generally results from a swelling of the synovial membranes, which is often idiopathic. Carpal tunnel syndrome can also be caused by pressure on the medial nerve from rheumatoid arthritis or edema in the final trimester of pregnancy.

Many instances of carpal tunnel syndrome can be treated conservatively, typically with a resting split and cortisone injection in to the carpal tunnel. However if the symptoms persist and/or reoccur, or if the patient has a severe sensory deficit or loss of function in thenar muscles, then surgical decompression of the nerve by release of the transverse carpal ligament is often indicated.

Commonly practiced surgical procedure for decompression of carpal tunnel ligament is accomplished by a longitudinal incision paralleling the thenar crease. The incision is carried down through the skin, subcutaneous fat, and palmar fascia to avoid the palmaris brevis muscle and then the transverse carpal tunnel ligament. Although the carpal tunnel is inspected, most cases do not require any surgical treatment within the carpal tunnel, other than the division of the ligament. Thereafter, the skin is sutured and the patient is splinted for approximately three weeks. A typical surgery requires approximately 20-25 minutes, including the dressing, and is performed as an outpatient.

The endoscopic carpal tunnel release instrument as described in U.S. Pat. Nos. 4,963,147; 4,962,770; 5,089,000; 7,628,798, US 2010/0228275 and 5,306,284 are comprised of a probes with dissecting devices, and endoscope attached to a camera for visualization. The probe is inserted in to the carpal tunnel through a small incision in the wrist. The scope inside the probe visualizes the transverse carpal ligament. Once the probe is properly placed the blade is raised inside the carpal tunnel dissecting the transverse carpal ligament from inside. This will result in decompression of carpal tunnel. This technique is more advantageous due to small incision resulting less trauma to the patient and faster recovery.

DESCRIPTION OF RELATED ARTS

U.S. Pat. Nos. 4,963,147; 4,962,770; 5,089,000; 7,628,798, US 2010/0228275 and 5,306,284, describe a surgical instrument which is used for Carpal tunnel release and is also useful in other surgical techniques and are incorporated herein as thought recited full. The instrument includes a probe with a cutting blade that houses an optical system. After the probe has been inserted in to the body cavity the cutting blade is extended through a lateral aperture in the probe to a position adjacent to the selected tissue, while allowing the tissue manipulation to be observed. The prior art surgical instrument, as illustrated in the above prior art patents, describes a cutting blade that extends through an axially fixed rotatable pivot pin. As an actuation shaft urges the cutting blade through the pivot pin, the distal end portion of the blade sweeps through an arc to reach a fully extended position. Initially the distal tip of the blade moves toward the distal end of the probe and then moves upwardly to its fully extended position. Once the blade is positioned properly under the transverse carpal ligament the hand piece is moved backward therefore dissecting the transverse carpal ligament from the distal end to proximal end.

SUMMARY OF THE INVENTION

A surgical instrument for endoscopic surgery having an endoscopic blade assembly. The assembly has a proximal connector to connect the blade assembly to a handle. A closed body is comprised of a top, opposing sides and a base and contains the blade mechanism and optical system. At the a distal end of the top of the body is an open region to enable a blade within the blade mechanism to extend beyond the body. The body can be manufactured from a solid or transparent bio-compatible material.

Open windows are placed on each of the opposing sides at distal end, proximate the open region. The open windows can be arcs or other configurations either open or with bars. When using bars, they are generally integral with the top and extend across the windows. The windows can extend from the top to the base or can extend only part way to the base. An integrated tissue retractor spring, once activated, extends above the open region. When not activated the integrated tissue retractor spring rests within an alcove within the open region. A bend in the integrated tissue retractor spring interacts with a groove in the blade mechanism drive shaft and the placement of the groove controls the activation of the spring in relation to activation of a blade. The spring is maintained within the body by a spring proximal tip that extends through receiving holes within each of the sides. A marking member, that can be in fluid contact with a marking reservoir, can be placed adjacent to the open region on the distal end of the body.

In another embodiment the body of the instrument can be curved with a proximal linear plane and a distal linear plane. The portion of the blade on the proximal linear plane, adjacent to the connector, is approximately 10 to 20% of the total usable length. The blade comprising the distal linear plane is connected to the portion of the blade on proximal linear plane by a curve. The curve is designed to provide approximately a 0.2 to 2 cm difference between the proximal linear plane and the distal linear plane. In this embodiment the blade shaft is manufacture from a flexible material.

In a further embodiment the handle has a linear body, said body containing a blade activation mechanism, at least one activation trigger, and connector means, said connector means receiving said proximal connector.

DESCRIPTION OF THE INVENTION

In general Endoscopy means looking inside and typically refers to looking inside the body for medical reasons using an endoscope, an instrument used to examine the interior of a hollow organ or cavity of the body. Unlike most other medical imaging devices, endoscopes are inserted directly into the organ. In a typical Endoscopic surgery endoscopes are inserted in to the body for visualization in combination with one or more surgical tools to manipulate and dissect tissue. In some surgical procedures such as carpal tunnel release the space is very limited and it is very beneficial to have the Endoscope and surgical tool to be combined to reduce trauma or injury to the surrounding nerves or other tissue.

Endoscopic carpal tunnel release instruments have been in the market for number of years. One of these instruments was designed based on U.S. Pat. No. 4,962,770 and U.S. Pat. No. 4,963,147. This surgical tool is used to inspect and manipulate selected tissue in a body cavity, and has particular application to performing carpal tunnel release procedure. These tools include a handle assembly, a probe member, an optical system, and a cutting system. The optical system and cutting system extend through the handle and into the probe and permit a surgical blade to be selectively deployed and retracted from a lateral opening in the top surface of the probe at its distal end. This instrument has been in the market for almost 20 years without any modifications and improvements.

Figure 1:
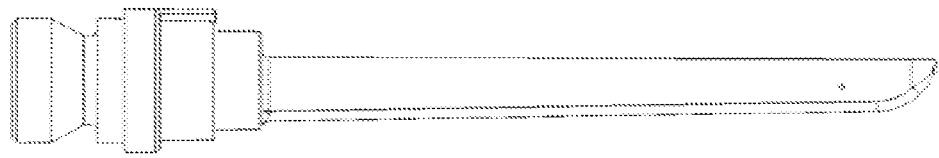
FIG. 1: is a perspective view of the cutting blade of a prior art device.
Figure 2:
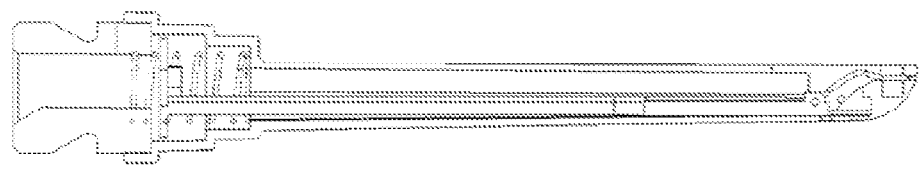
FIG. 2 is a cutaway side view of the prior art device of FIG. 1.

The present invention provides a more accurate and safer means for endoscopic surgery, and has particular application to performing safe and effective carpal tunnel release. One of the key problems with the predominantly used prior art device is the narrow window of visualization during the procedure due to the sidewalls of the device, as illustrated in FIGS. 1 and 2. This narrow visualization window limits surgeon's field of view during the procedure and creates possible risk for accidental damage to the surrounding anatomical structures, for example cutting of the medial nerve during a carpal tunnel procedure.

For description, reference will be made to carpal tunnel syndrome and the dissection of the transverse carpal ligament. It will be clear to those skilled in the art upon reading the description, how the device would be advantageous in other areas of endoscopic surgery.

Figure 3:
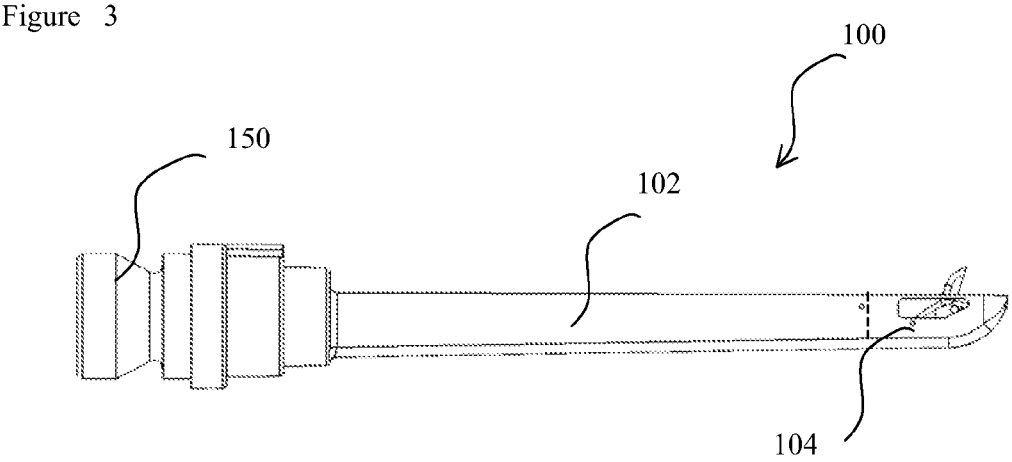
FIG. 3: is a side view of one embodiment of the endoscopy assembly having cut out sections to increase visibility, in accordance with the present invention.

In FIG. 3 the disclosed endoscopic blade assembly 100 is shown with the blade housing 102 extending from the connector 150 that leads to the handle (not shown). For accuracy of description, reference will be made to the distal section 104 of the blade housing 102 however the distal section 104 is a part of the blade housing 102 and the division is merely a reference point. It should also be noted that the connector 150 and blade housing 102 can be used with any design handle, such as trigger style handles or the disclosed straight handle. Whether the incision device 100 is integral to or separate from the handle, disposable or reusable is strictly dependent upon manufacture preference and does not affect he disclosed design with the exception of the means of connection. Connector 150 is shown as a cylindrical shape, however the connector 150 can also be shaped to various geometrical shapes and matched with the handle connection cavity.

Figure 4:
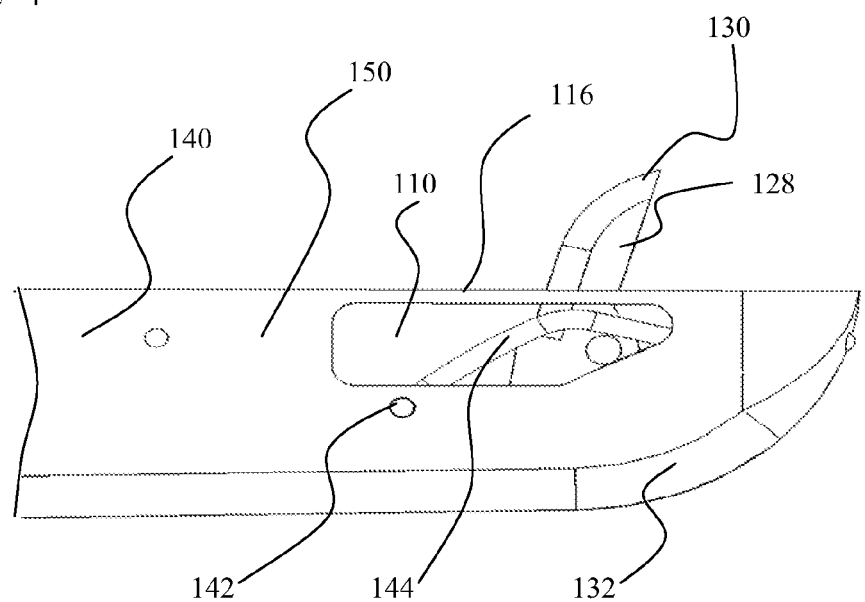
FIG. 4 is a side view of the tip of the endoscopy assembly of FIG. 3 in accordance with the present invention.
Figure 5:
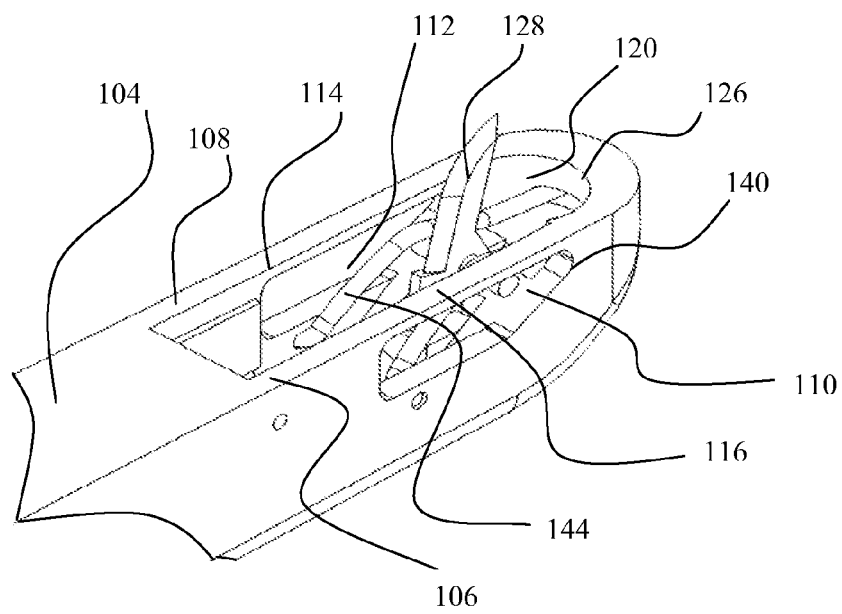
FIG. 5 is a perspective view of the tip of the endoscopy assembly of FIG. 3 in accordance with the present invention.

In order to create a wider visualization angle on the distal section 104 of the blade housing 102, the side walls 106 and 108 have been modified to have windows, or cutout sections, 110 and 112 respectively as shown clearly in FIGS. 4 and 5.

The windows 110 and 112 can be supported by thin plastic or metal bars 114 and 116 to provide additional structural support for the blade housing side walls 106 and 108. The additional structural support is only necessary in some applications and their use for support will be evident to those skilled in the art. The use of the bars 114 and 116 further prevents tissue from falling in to the distal opening 120 of blade housing 102.

The windows 110 and 112 can also be placed on the blade assembly 102 without the use of support bars 114 and 116

In the disclosed blade assembly 102 (FIG. 3) the windows 110 and 112 preferably have a distal end 140 that starts about 0-5 mm from the interior surface 126 of the distal opening 120. Although the windows 110 and 112 distal end 140 can be a further distance from the interior surface 126, a change that could be applicable in some applications, the 0-5 mm provides the greatest visibility increase. The windows 110 and 112 can have a length of about 2-15 mm longitudinally toward the connector 150 and generally have a length substantially equal to the length of the distal opening 120. As an example, to provide the desired visibility for a device used to treat carpal tunnel, the windows 110 and 112 would be in the range of about five (5) to twenty (20) millimeters.

Figure 6:
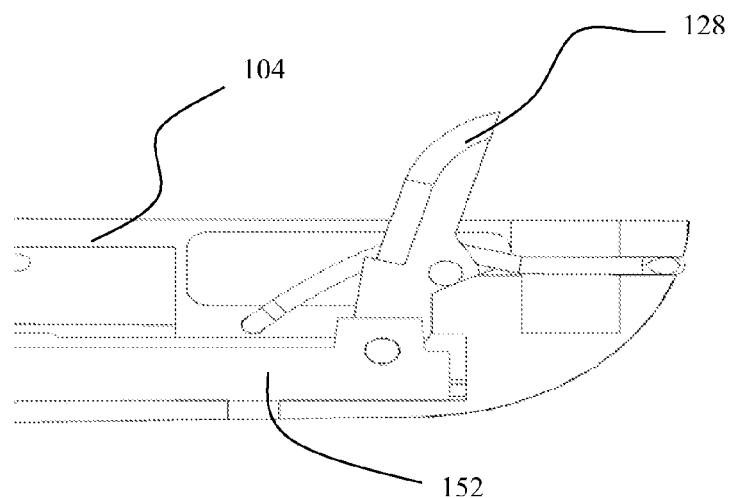
FIG. 6 is a cutaway side view of the assembly of FIG. 3 in accordance with the invention.

The height, or thickness of the support bars 114 and 116 can be approximately about 0.1-4-mm The windows 110 and 112 can extend completely to the base 132 of the blade assembly 102 or as far toward the base 132 is required for enhanced visibility. As illustrated in FIG. 6, the blade shaft 152 runs along the base of the assembly 102 to operate the blade 128. As disclosed in detail U.S. Pat. No. 5,306,284 as well as other patents in the art.

The configuration of the windows 110 and 112 can be designed in various geometric shapes such as circular, oval, rectangular or triangular. It should be noted that the above dimensions are for example only and someone skilled in the art would be aware of the length and depth of the windows in proportion to the body of the blade assembly in order to prevent compromising structural integrity.

By placing the windows 110 and 112 in line with the distal opening 120, visualization for the entire field of view and blade 128 movement during the surgery as observed by surgeon is enhanced greatly. By extending the windows 110 and 112 at least to the distal end 130 of the blade 128 when in the retracted position, the visualization field of view is increased by 30-40%. The increased visibility is illustrated hereinafter in FIGS. 22 and 23.

Depending upon the application, both the windows 110 and 112 as well as the distal opening 120 can require enlarging. The blade 128 is assisted by a spring 144 As disclosed in the prior art, the spring helps in lifting the blade in a more vertical direction during use. The spring 144 is secured to the distal end 104 at securing points 142. The securing point 142 can be moved proximally by lengthening the spring 144 to create desire distance to enable enlargement of the viewing area.

Another problem encountered by surgeons with prior art disposable blade assemblies is the visibility and operation of the blade during procedures. For example in some cases during the dissection of the transverse carpal ligament as the ligament is dissected, the fat pad on top of the ligament falls inside the blade housing opening at the distal end. This limits, or completely blocks, the visualization field and function of the blade mechanism. This problem is magnified in obese patients with excessive body fat content.

Figure 7:
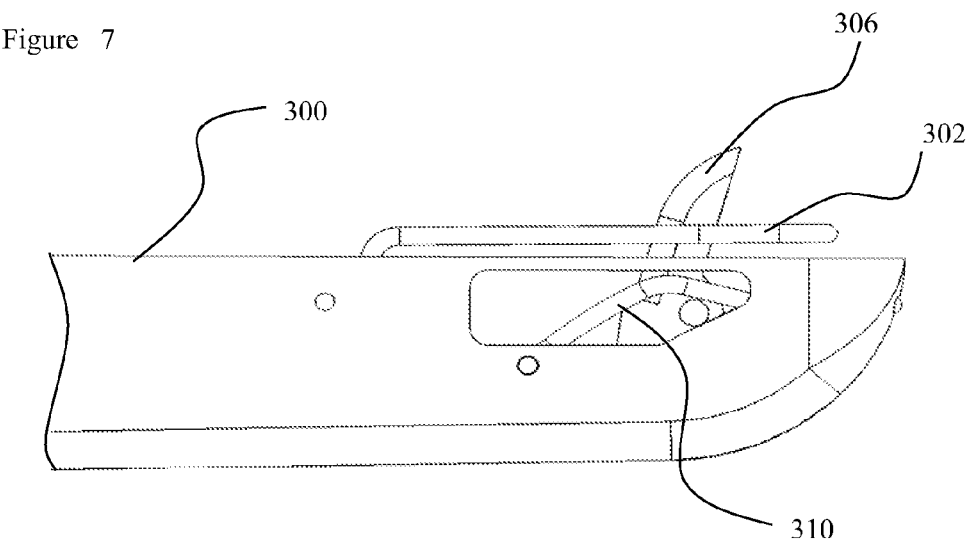
FIG. 7 is a side view of an additional embodiment of a blade assembly having cut out sections and an integrated tissue retractor spring in accordance with the present invention.
Figure 8:
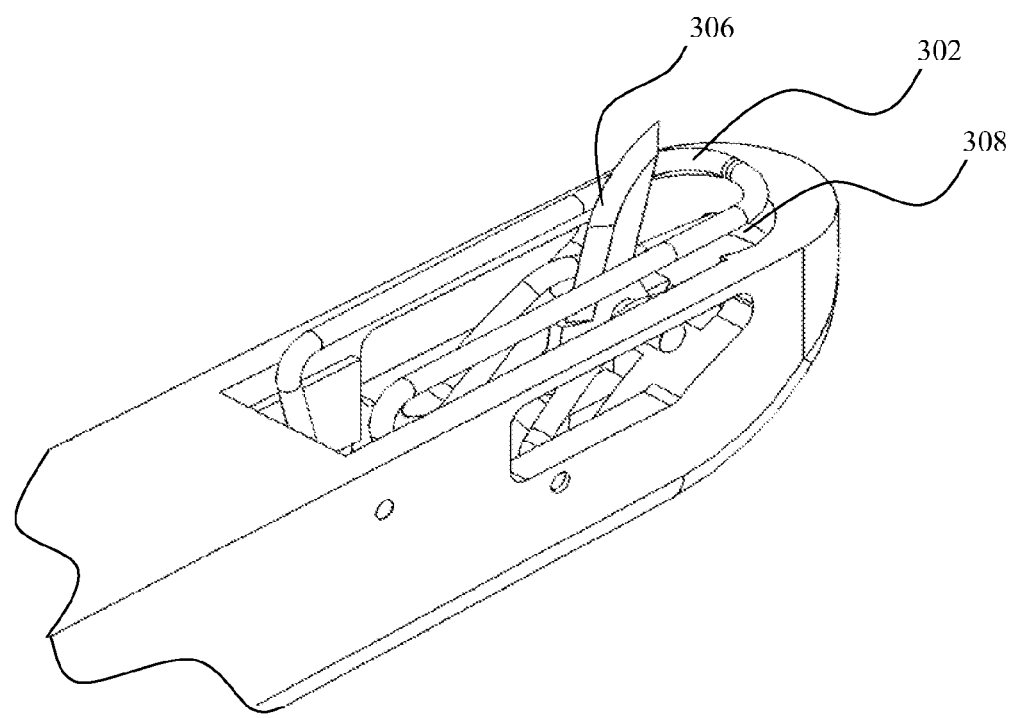
FIG. 8 is a perspective view of the blade assembly of FIG. 7 in accordance with the present invention.

To resolve this problem, an integrated tissue retractor spring 302 as illustrated in FIGS. 7 and 8 is placed into the blade assembly 300. This integrated tissue retractor spring 302 is preferably securely placed in the housing 300 in a manner that it will not increase overall blade assembly housing 300 height and width, although in some applications a slight increase can be tolerated. The integrated tissue retractor spring 302 is preferably dimensioned to fit within an alcove 308 and automatically rises from the alcove 308 upon activation of the blade 306. The integrated tissue retractor spring 302 provides uniform and upward force on the interior surface of the transverse carpal ligament, or other tissue, during the procedure. The interaction between the integrated tissue retractor spring 302 the blade 306 and the cutting shaft (not shown) is described in detail further hereinafter.

Although the construction of the exterior of the blade assembly varies in the embodiments using the integrated tissue retractor spring, the internal interaction between the, blade, shaft and other interior elements remains the same.

Figure 9:
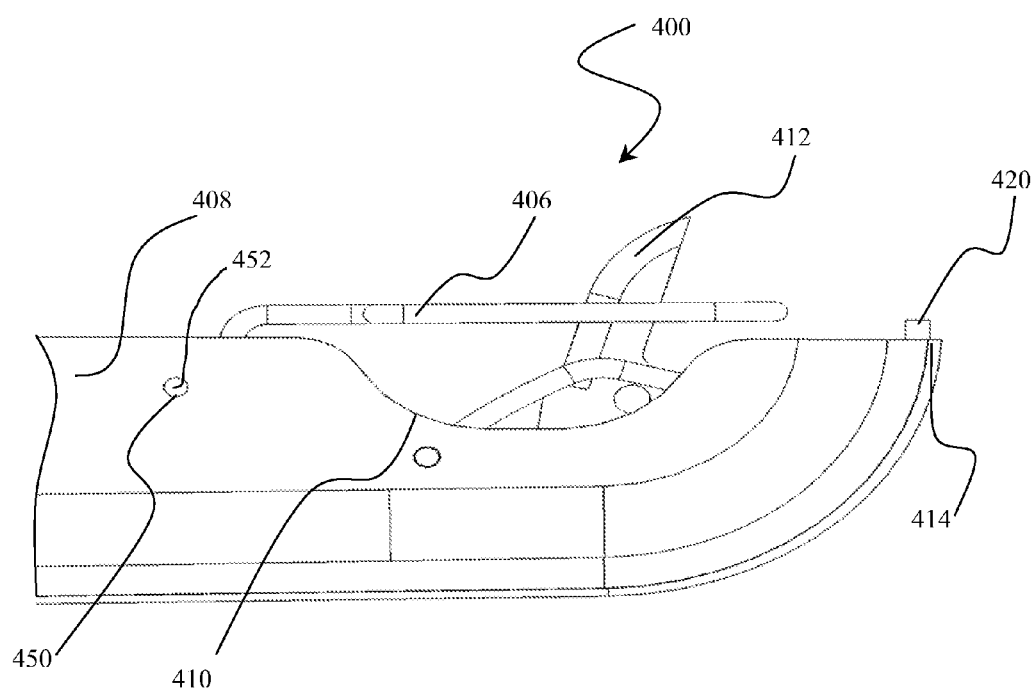
FIG. 9 is side view of an embodiment of the blade assembly having arced sides and incorporating the integrated tissue retractor spring and marking member in accordance with the present invention.
Figure 10:
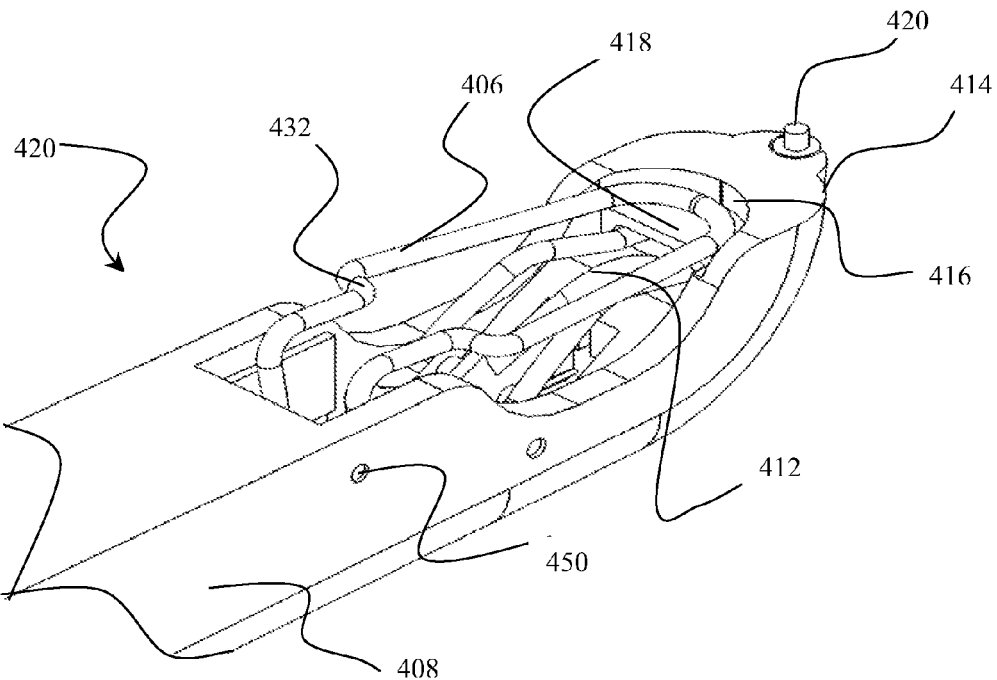
FIG. 10 is a perspective view of the embodiment of FIG. 9 in accordance with the present invention.

In general surgeons have been trained to mark surgical and incision sites prior to dissection. This practice helps the surgical planning as the surgeon identifies critical anatomy prior to the procedure. This issue is very critical in endoscopic carpal tunnel release procedure since the surgeon is operating in a very limited space with several key anatomical structures in close vicinity. As illustrated in FIGS. 9 and 10 the blade housing 408 of the blade assembly 400 can incorporate a marking member 420 within the distal end 414 of the housing 408. The marking member 420 can be deployed using a second trigger 460 (FIG. 15) in the hand piece or the same trigger used for blade deployment or other through other applicable means. The marking member 420 is pushed up at the distal end 414 of the blade housing 408 to create a line on the tissue, such as the transverse carpal tunnel ligament, prior to dissection. The marking member can be in fluid contact with a reservoir of bio-compatible marking material to maintain the marking member 420 small. In some embodiments, the marking member 420 can contain all the necessary marking material and the need for a reservoir will be evident to those skilled in the art. This line is visually inspected prior to deployment of the blade and dissection of transverse carpal ligament, thereby enabling the surgeon to ensure that no nerves or excess tendon will be cut.

In FIG. 9 the integrated tissue retractor spring 406 and the blade 412 have been partially extended. In FIG. 10 the blade 412 and tissue integrated tissue retractor spring 406 are in the fully retracted position. The alcove 416 is clearly illustrated in this Figure showing the recessed area dimensioned to receive the integrated tissue retractor spring 406. The alcove 416 has a base 418 on which the integrated tissue retractor spring 406 rests in the retracted position. The base must be of sufficient depth to provide support for the lift spring 406 but not interfere with the lift of the blade 412. As seen, the integrated tissue retractor spring 406 has a bend 432 that brings the spacing between the two legs in to fit within the housing 408. The integrated tissue retractor spring described here can also be deployed using a combination of mechanisms in the blade housing and hard piece.

In FIG. 10 the blade 412 and integrated tissue retractor spring 406 are in the recessed position used for entry into the body. The end of the integrated tissue retractor spring 406 is resting on the base 418 within the alcove 416.

Figure 11:
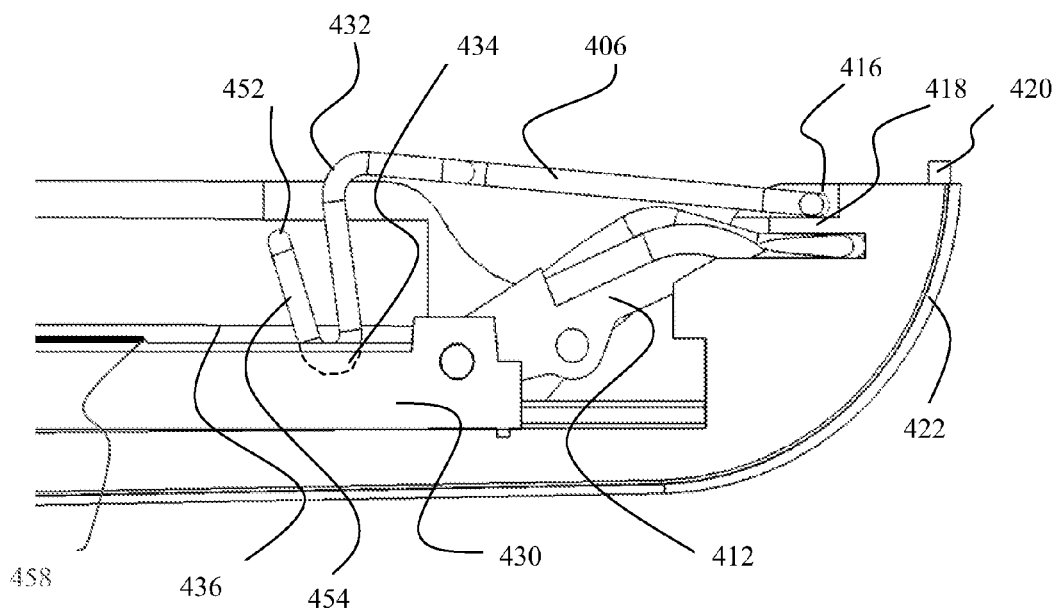
FIG. 11 is a cutaway side view of the blade assembly of FIG. 10 with the blade and integrated tissue retractor spring in the retracted position in accordance with the present invention.

In FIG. 11 the blade housing 408 is illustrated with one side cut away to more clearly see the blade cutting shaft 430 that serves to move the blade 412 to the cutting position. Also illustrated in this figure is the connection between the bend 434 of the integrated tissue retractor spring 406 and the blade shaft 430. It is through this interaction that the blade shaft 430 activates both the blade 412 and the integrated tissue retractor spring 406. A groove, or notch, 436 is placed in the blade shaft 430 to receive the spring bend 434. Although a groove is illustrated herein, it will be obvious to one skilled in the art where to place a notch to obtain the desired blade/spring interaction. The length of the groove 436 will determine how rapidly and how far the integrated tissue retractor spring 406 rises. As the blade shaft 430 moves the blade 412 to the upright position the groove end 458 approaches the bend 434 and, once in contact with the bend 434 the groove end 458 rotates the integrated tissue retractor spring 406 around the proximal tip 452. To maintain the integrated tissue retractor spring 406 in position and the ability to rotate, the proximal tip 452 of the integrated tissue retractor spring 406 extends at right angles from the leg 454 and is dimensioned to fit into the receiving hole 450. This design should be considered an example and other methods of rotating the spring can be used. This spring can be made from various medical grades of stainless steel (300 series), or other applicable materials, and pre-shaped and heat treated to fit in the space Also is illustrated is the marking channel 422 that contains the marking substance fed to the marking element 420.

Figure 12:
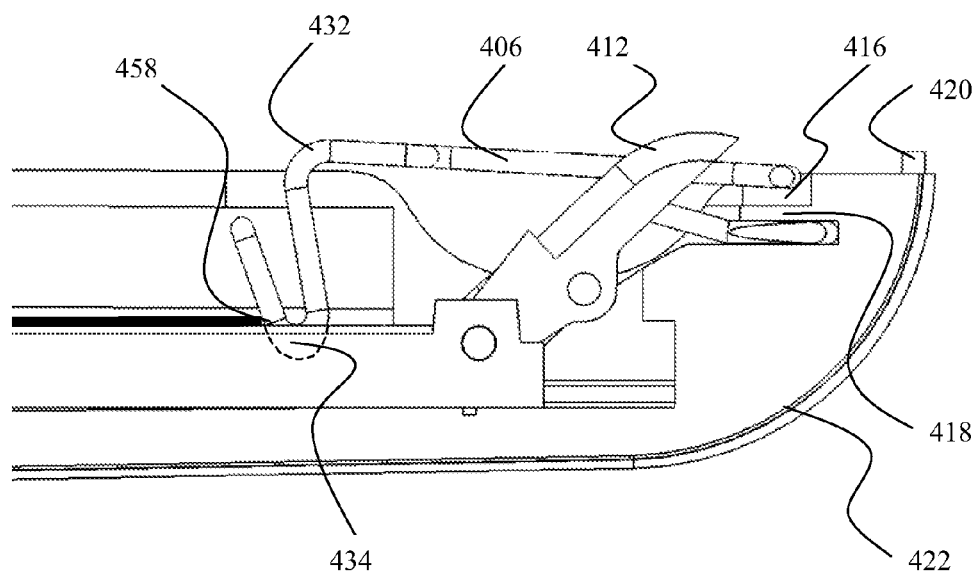
FIG. 12 is a cutaway side view of the blade assembly of FIG. 10 with the blade and integrated tissue retractor spring in the partially extended position in accordance with the present invention.
Figure 13A:
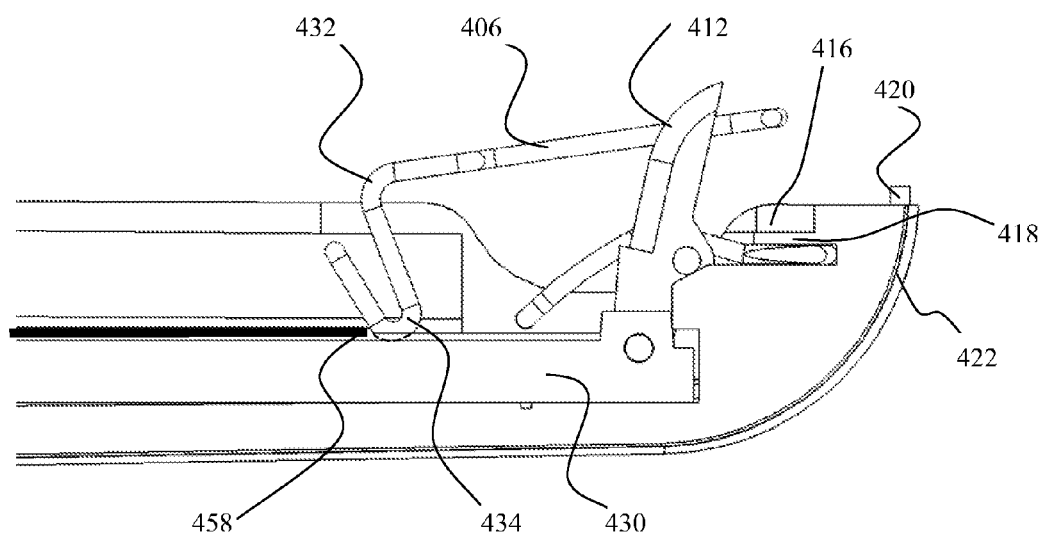
FIG. 13A is a cutaway side view of the blade assembly of FIG. 10 with the blade and integrated tissue retractor spring in the fully extended position in accordance with the present invention.
Figure 13B:
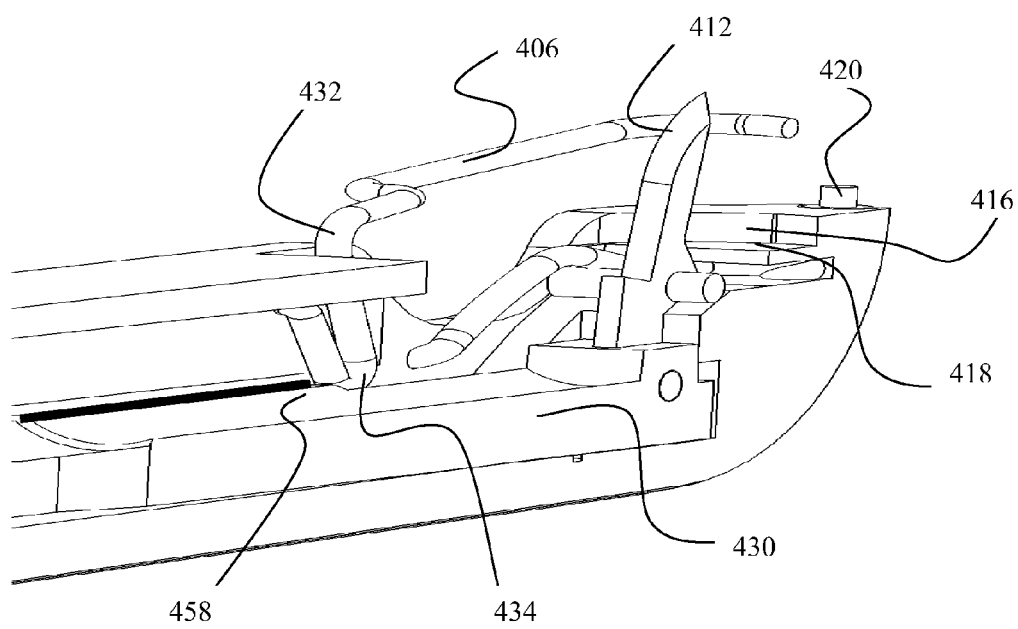
FIG. 13B is a cutaway perspective view of the blade assembly in FIG. 13 with the blade and Integrated tissue retractor spring in the fully extended position in accordance with the present invention.

In FIGS. 12 and 13 A-B the blade 412 and integrated tissue retractor spring 406 are illustrated in a partially erect and fully erect position. It should be noted that in these figures the integrated tissue retractor spring 406 follows the blade 412, however, by changing the location of the groove 436 on the blade shaft 430, the timing between the two elements can be changed. In these figures the groove 436 is not seen as the groove end 458 is in contact with the spring bend 434.

Figure 14:
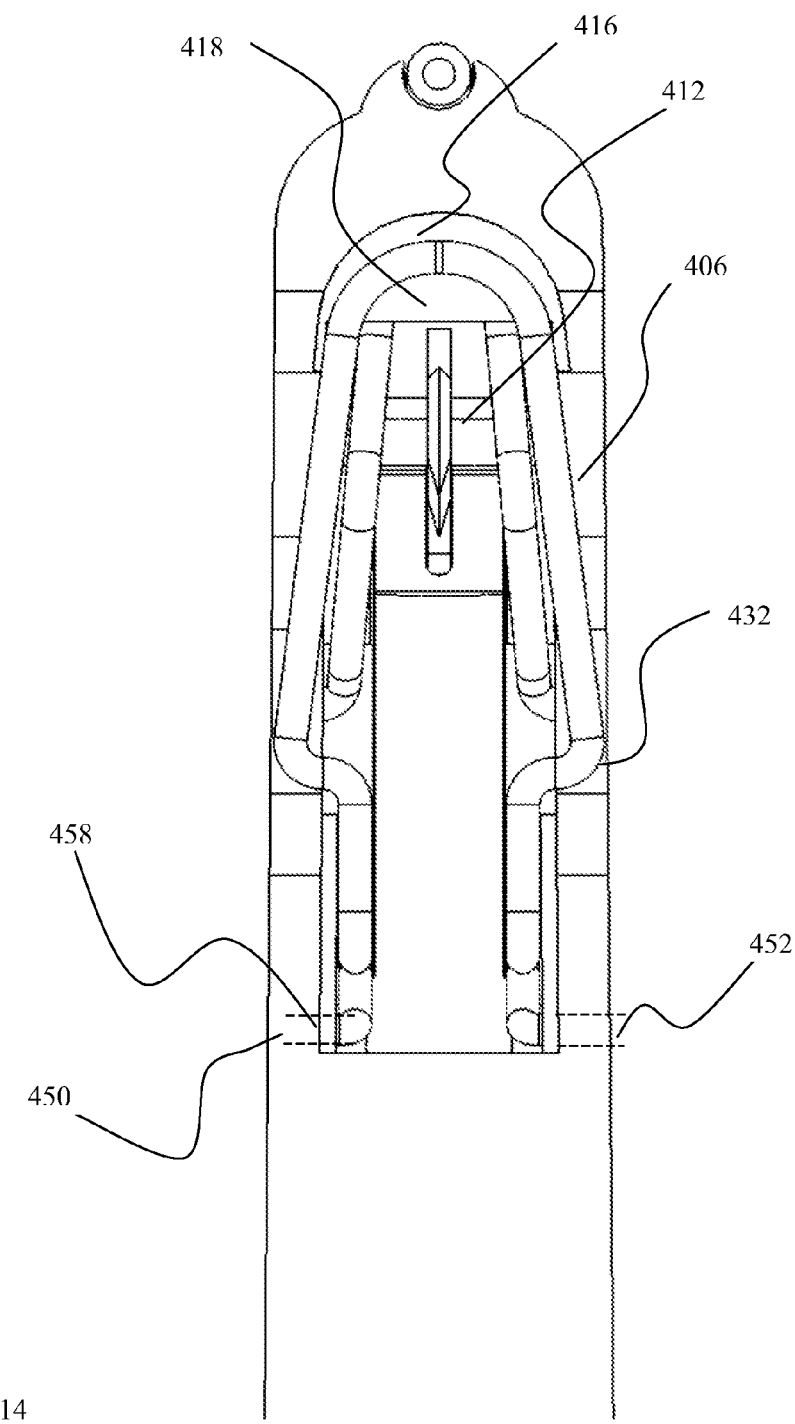
FIG. 14 is a top view of the blade assembly of FIG. 10 in accordance with the present invention.

The positioning of the elements is further illustrated in FIG. 14 showing the integrated tissue retractor spring 406 and the bend 432 and dimensioning within the alcove 416 and base 418. The positioning of the blade 412 and marking element 420 with respect to other elements are also clearly illustrated in this Figure. The proximal tip 452 can be seen in this figure extending from the leg 458 to the receiving hole 450.

Figure 15:
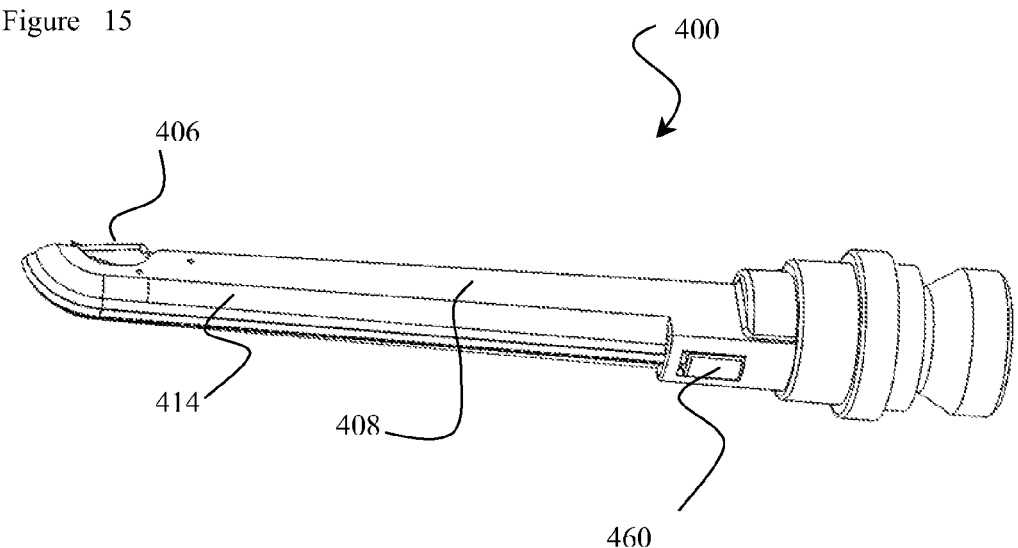
FIG. 15 is a perspective view of a blade assembly showing the marking member activation means in accordance with the present invention.
Figure 16:
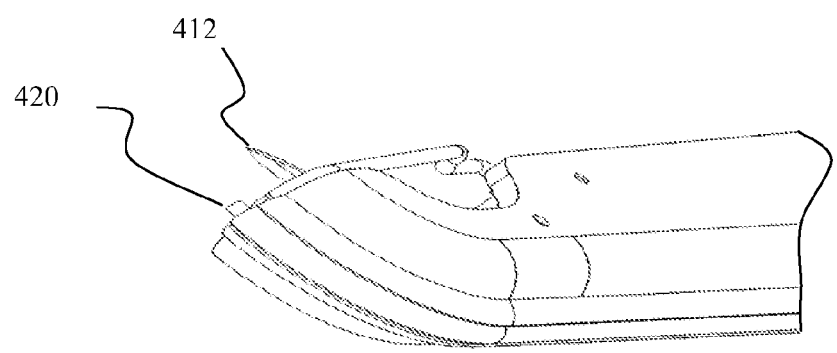
FIG. 16 is a perspective view of the marking member and fully extended blade in accordance with the present invention.

In FIG. 15 the cutting blade assembly 400 is illustrated showing the marking element activation button 460. As seen in this and FIG. 16, the sides of the assembly are cut and the integrated tissue retractor spring 412 is in used. In FIG. 16, the blade 412 is extended above the marking element 420.

As stated heretofore, all elements are interchangeable and the activation button 460, marking element 420 and lift spring 406 can be used with any housing configuration herein.

Figure 17:
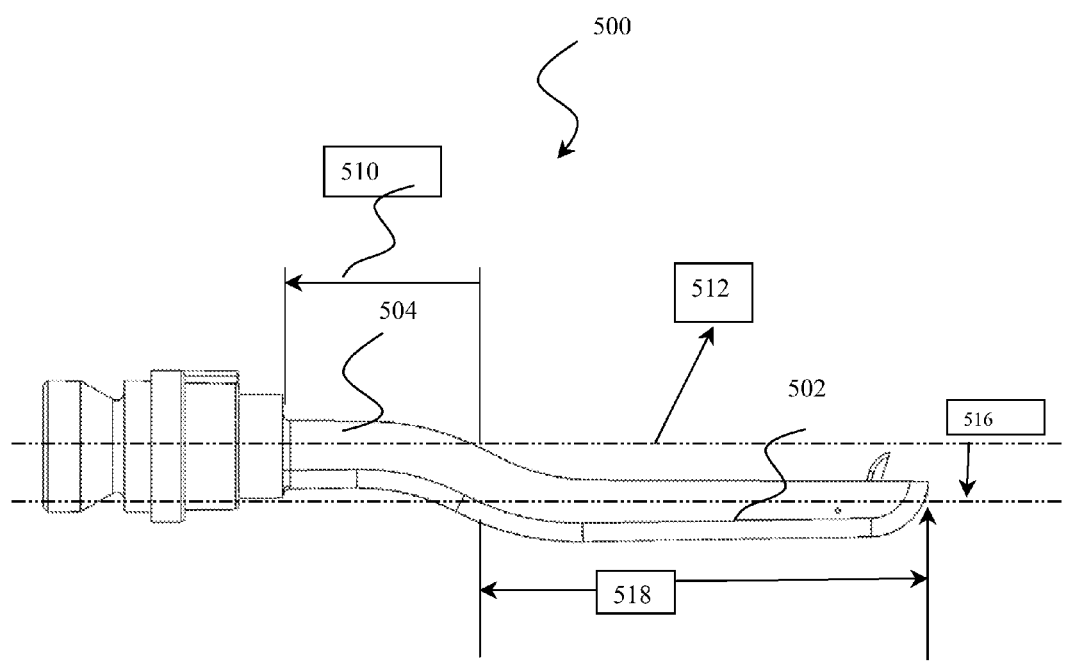
FIG. 17 is a side view of a curved blade assembly in accordance with the present invention.

To facilitate use in applications such as carpal tunnel, the above elements can be incorporated on a curved blade assembly 500 as illustrated in FIG. 17. As seen in this view, the blade assembly 500 is curved, dropping the distal end 502 from the proximal end 504. This enables the user's hand to clear the patient's forearm, or other body part, during use, with the drop being dependent upon the end use. For example, when using an assembly having a blade usable length of 6.5 Cm, the distal end 502, approximately 80% to 90% (518) of the blade length, would be dropped in the lower plane, approximately 0.2 to 2 Cm while the proximal portion 510 would having a center line 512 along the centerline of the connector. This can be further described as the centerline 516 of the distal portion 502 drops from the centerline 512 of the proximal portion 504 approximately about 0.2 to 2 cm, depending upon end usage. In most applications the proximal portion 504 is about 1 to 2 cm, again depending upon application. However, as stated, the length of the blade and drop would be end use dependent and known to those skilled in the art.

The curve blade housing assembly 500 raises the position of the hand piece to a higher plane resulting in less interference with the patient's forearm. This enhancement can be made with utilization of flexible endoscope. The curved blade housing assembly can be incorporated in to the fully disposable pistol grip housing or the disclosed In-Line housing design.

The blade housing 500 is manufactured from a clear material that enables the surgeon to see through the walls, thereby eliminating the need for the cutouts disclosed heretofore. However, it should be noted that the clear material can also be used with the cutouts, dependent on preference.

The endoscopic carpal tunnel release system used in the prior art includes a hand piece and disposable blade and endoscope. The endoscope and disposable blade assembly is assembled in to the hand piece prior to surgery. This can be a time consuming and somewhat complicated process. The incorrect assemblies of these components are due to the improper training of the surgical staff and can lead to malfunction during the surgery. Enhancement can be made to this device to incorporate the hand piece and blade in to one disposable assembly, thereby eliminating a critical step in the assembly of this instrument. The disclosed device has a full disposable blade housing assembly with hand piece. This will be a single-use sterile package device that will only require the insertion of scope. This will also eliminate additional cost for sterilization processing of the hand piece by the hospital staff. The current hand piece for the device is pistol grip, and is, by its nature, hard to maneuver as the surgeon tries to position the blade assembly.

Figure 18:
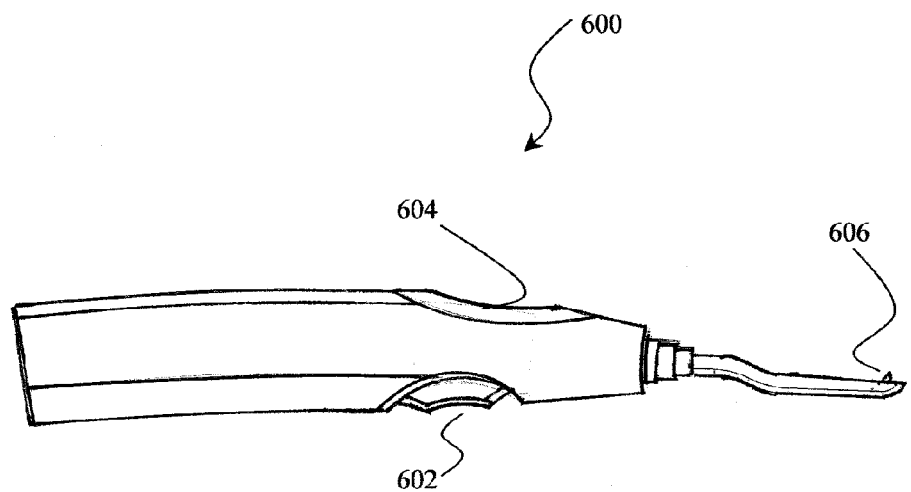
FIG. 18 is a rotated side view of an In-Line hand piece in combination with the curved blade assembly of FIG. 17 in accordance with the present invention.
Figure 19:
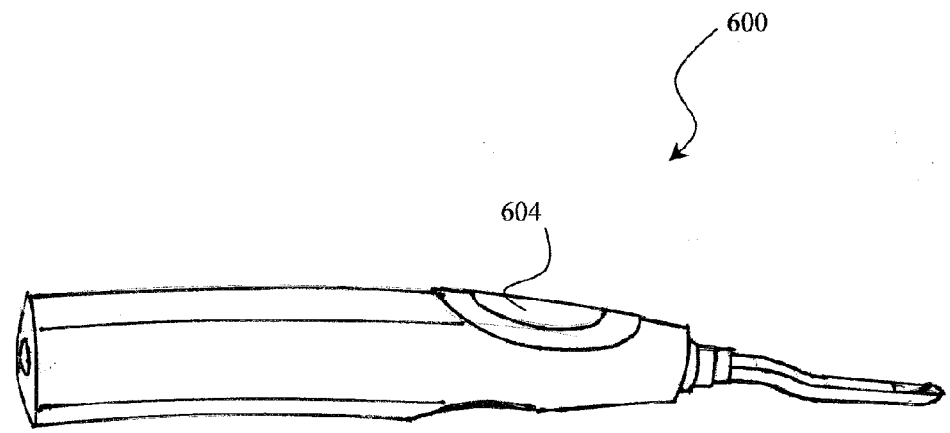
FIG. 19 is a side view of an In-Line hand piece in combination with the curved blade assembly of FIG. 17 in accordance with the present invention.

FIGS. 18 and 19 illustrate the disclosed In-Line handle device 600 with trigger 602 and thumb rest 604. The trigger 602 is positioned for easy blade deployment by the surgeon's index. or other, finger, thereby dramatically enhancing the functionality of this device. The internal mechanism (not shown) to activate the blade 606 can be any design that is compatible with the end result and would be known to those skilled in the art.

As the blade 500 is curved, the material of manufacture for the interior blade shaft must be manufactured from a flexible plastic in order to properly function.

As can be seen from the description above, the in-line device can be fully disposable, except for the scope, or the handle can be a permanent tool with only the blade assembly being disposable.

Figure 20:
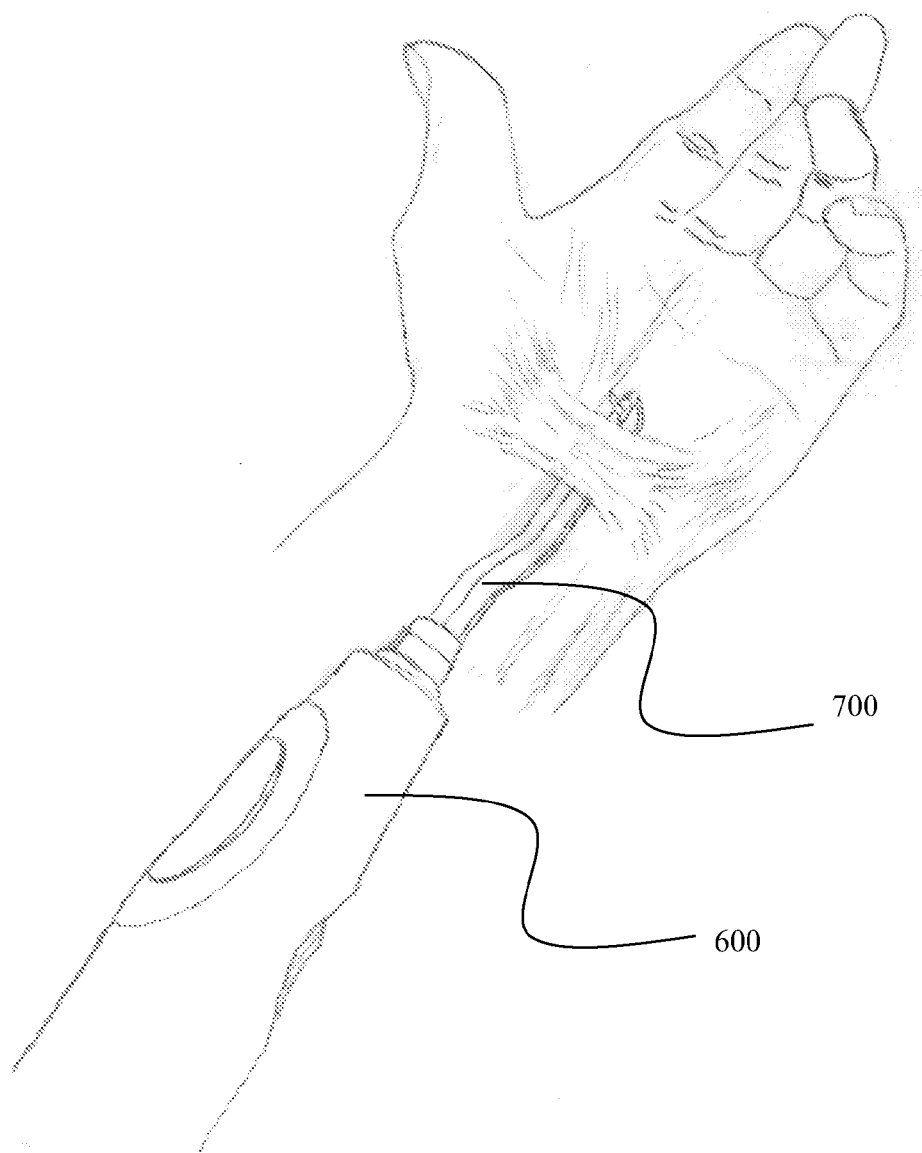
FIG. 20 is a phantom view of the in-line hand piece in combination with curved blade inserted into the hand of the patient in accordance with the present invention.

As is illustrated in FIG. 20, the In-line handle 600 in combination with the curved blade 500 mitigates much of the difficulty of manipulating the blade housing assembly 500 during the carpal tunnel surgery. With the disclosed handle 600 and housing assembly 500 during insertion, the handle 600 is aligned with the patient forearm.

Figure 21:
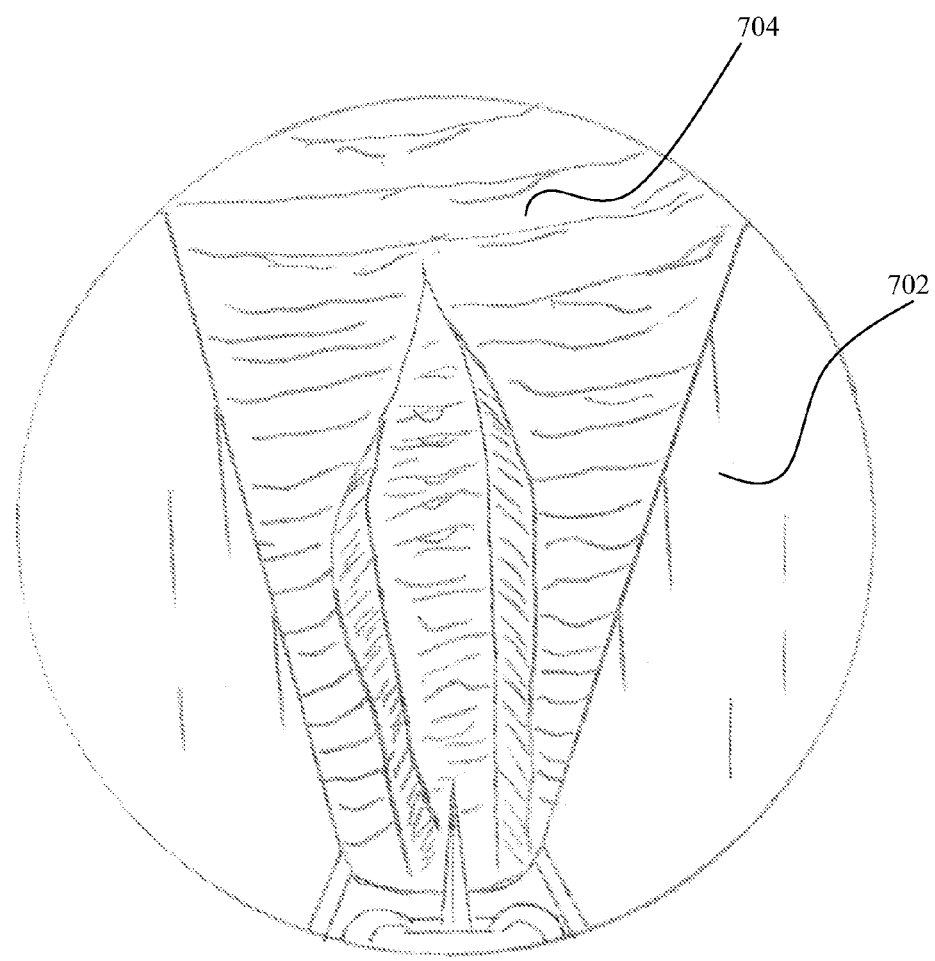
FIG. 21 is a view of the surgeon's visibility during a carpal tunnel release procedure using a prior art device.

FIG. 21 illustrates the field of view through the scope as observed by the surgeon using prior art devices. The prior art disposable blade housing side walls 702 block a large section of field of view as surgeon views the transverse carpal ligament 704.

Figure 22:
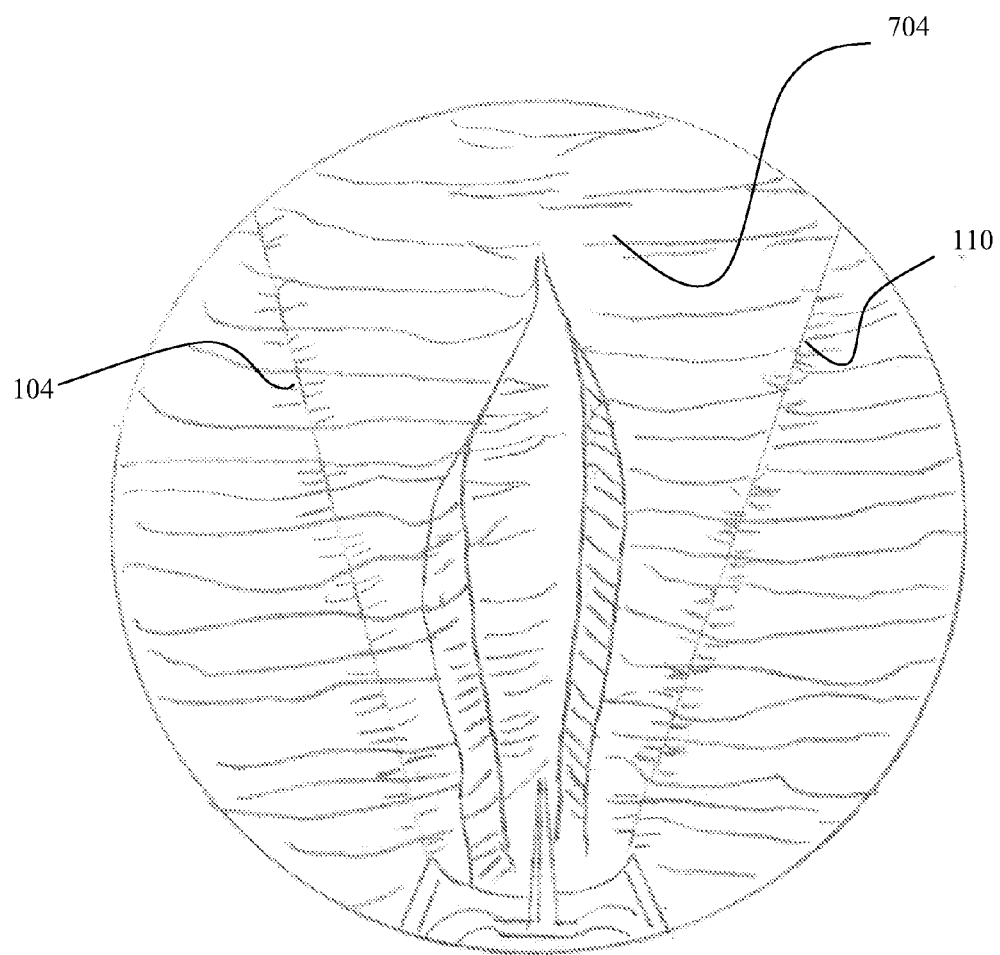
FIG. 22 is a view of the surgeon's visibility during a carpal tunnel release procedure using the disclosed assembly having a transparent body in accordance with the present invention.

FIG. 22 illustrates the field of view through the scope as observed by surgeon using the disclosed device 400 having cut sections 110 and 112 in the housing 104. The transverse carpal ligament 704 can be observed well beyond the boundaries of the disposable blade housing 104. The supporting metal or plastic bars 114 and 116 prevent the ligament and fat from dropping in to the visual field and provide structural support for the disposable blade housing 104. As can be seen from this figure, the supporting bars 114 and 116 do not obstruct the surgeon's view. When using the disclosed device with transparent walls, the thin line created by the supporting bars 114 and 116 would be eliminated.

Figure 23:
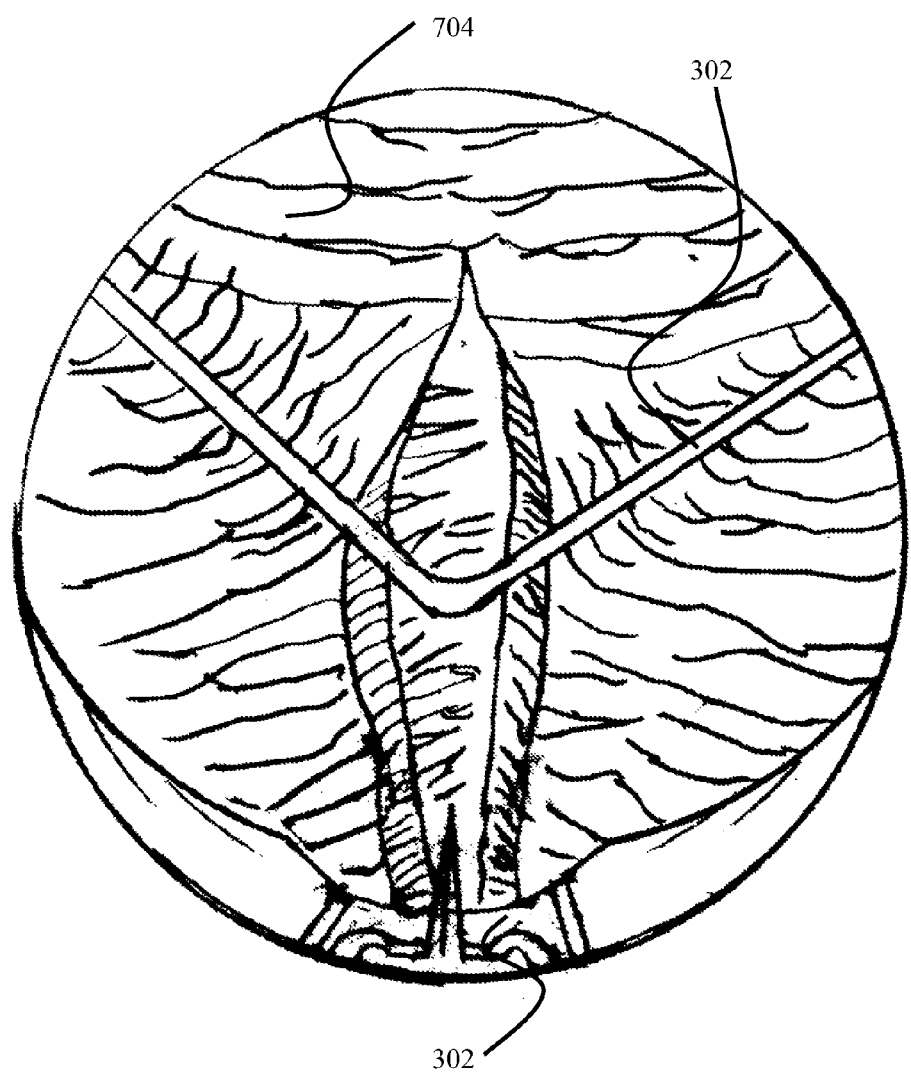
FIG. 23 is a view of the surgeon's visibility during a carpal tunnel release procedure using the disclosed assembly in accordance with the present invention.

In FIG. 23 the lift spring 302 is illustrated holding up the tissue as the blade 306 cuts through the ligament 704. As can be seen, the lift spring 302 does not obstruct the surgeon's view.

An alternative method of achieving greater visibility is by molding the disposable blade housing from a clear, translucent plastic, with or without the use of the cut section 102.

BROAD SCOPE OF THE INVENTION

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims (e.g., including that to be later added) are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language of the present invention or inventions should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example."

What is claimed is:

1. A surgical instrument for endoscopic surgery having an endoscopic blade assembly, said blade assembly having
   a. a proximal connector, said connector enabling said blade assembly to be connected to a handle;
   b. a closed body, said closed body having a top, opposing sides, a distal end and a base opposite said top and containing a blade mechanism and optical system;
   c. an open region on said top at said distal end; said open region enabling a blade within said blade mechanism to extend beyond said top of said closed body and providing said optical system unobstructed visibility through said top;
   d. open windows on each of said opposing sides and extending from proximate said top toward said base, said windows providing said optical system unobstructed visibility through said opposing sides;
   e. an integrated tissue retractor spring, said spring being configured to lie within said open region until activated and once activated extending above said open region to support tissue during dissection;
   f. a blade activation shaft within said blade mechanism, said blade activation shaft having a groove to receive a bend in said spring.

2. The instrument of claim 1 further comprising bars, said bars extending across said windows to said distal end and being on a same plane as said top, said bars having a thickness of approximately about 0.1-4 mm.

3. The instrument of claim 1 further comprising an alcove within said distal end of said open region to receive and support said spring when not activated.

4. The instrument of claim 1 wherein placement of said groove controls activation of said spring in relation to activation of said blade.

5. The instrument of claim 1 wherein said spring is maintained within said body by a spring proximal tip that extends through receiving holes within each of said sides.

6. The instrument of claim 1 further comprising a marking member, said marking member being adjacent to said open region on said distal end of said closed body.

7. The instrument of claim 6 wherein said marking member is in fluid contact with a marking reservoir.

8. The instrument of claim 1 wherein said closed body has a proximal linear plane and a distal linear plane and a centerline, said centerline being between and parallel with, said proximal linear plane and said distal linear plane, said proximal linear plane and said distal linear plane being parallel to one another and offset from opposing sides of said centerline and connected by a curve to provide approximately an offset of about 0.2 to 2 cm between said proximal linear plane and said distal linear plane to place said distal linear plane in contact with said tissue and said proximal linear plane elevated above said tissue.

9. The instrument of claim 8 wherein said blade activation shaft is flexible.

10. The instrument of claim 1 wherein said closed body is transparent.

11. A surgical instrument for endoscopic surgery having an endoscopic blade assembly, said blade assembly having:
   a. a proximal connector, said connector enabling said blade assembly to be connected to a handle;
   b. a closed body, said closed body having a substantially flat top, opposing sides, a distal end and a curved base and containing a blade mechanism having a blade shaft and optical system;
   c. an open region on said top at said distal end, said open region enabling a blade within said blade mechanism to extend beyond said substantially flat top of said closed body and provide said optical system unobstructed visibility;
   d. open windows on each of said opposing sides and extending from said top toward said base, said windows providing said optical system unobstructed visibility through said opposing sides;
   e. an integrated tissue retractor spring, said spring being configured to lie within said open region until activated by said blade mechanism and once activated extending above said open region to support tissue away from said blade during dissection,
   f. a blade activation shaft within said blade mechanism, said shaft having a groove to receive a bend in said spring and placement of said groove controls activation of said spring in relation to activation of said blade, said spring being maintained within said body by a spring proximal tip that extends through receiving holes within each of said sides.

12. The instrument of claim 11 wherein said closed body has a proximal linear plane and a distal linear plane and a centerline, said centerline being between and parallel with, said proximal linear plane and said distal linear plane, said proximal linear plane and said distal linear plane being parallel to one another and offset from opposing sides of said centerline and connected by a curve to provide approximately an offset of about 0.2 to 2 cm between said proximal linear plane and said distal linear plane to place said distal linear plane in contact with said tissue and said proximal linear plane elevated above said tissue.

13. A surgical instrument for endoscopic surgery having an endoscopic blade assembly, said blade assembly having
   a. a proximal connector, said connector enabling said blade assembly to be connected to a handle;
   b. a predominately closed body, said closed body having a top, opposing sides, a distal end and a base and containing a blade mechanism having a blade activation shaft and optical system;
   c. an open region on said top at said distal end, said open region enabling a blade within said blade mechanism to extend beyond said top of said closed body and provide said optical system unobstructed visibility through said top;
   d. open windows on each of said opposing sides and extending from said top toward said base, said windows providing said optical system unobstructed visibility through said opposing sides;
   e. an integrated tissue retractor spring, said spring being configured to lie within said open region until activated and once activated extend above said open region to support tissue away from said open region during dissection, said tissue retractor spring being activated in response to activation of said blade mechanism, wherein said blade activation shaft has a groove to receive a bend in said spring.

14. The instrument of claim 13 further comprising an alcove within a distal end of said open region to receive and support said spring when not activated.

15. The instrument of claim 13 wherein placement of said groove controls activation of said spring in relation to activation of said blade.

16. The instrument of claim 13 wherein said spring is maintained within said body by a spring proximal tip that extends through receiving holes within each of said sides.

* * * * *